(12) United States Patent
Bernstein

(10) Patent No.: US 8,168,214 B2
(45) Date of Patent: May 1, 2012

(54) LOCAL ADMINISTRATION OF GALLIUM COMPOSITIONS TO TREAT PAIN

(76) Inventor: Lawrence R. Bernstein, Menlo Park, CA (US)

( * ) Notice: Subject to any disclaimer, the term of this patent is extended or adjusted under 35 U.S.C. 154(b) by 789 days.

(21) Appl. No.: 11/936,607

(22) Filed: Nov. 7, 2007

(65) Prior Publication Data

US 2008/0113004 A1     May 15, 2008

Related U.S. Application Data

(60) Provisional application No. 60/858,182, filed on Nov. 9, 2006.

(51) Int. Cl.
*A61K 33/34* (2006.01)
*A61K 15/16* (2006.01)
*A61K 9/20* (2006.01)
*A61K 9/68* (2006.01)
*A61K 9/28* (2006.01)
*A61K 9/12* (2006.01)
*A61P 17/00* (2006.01)

(52) U.S. Cl. ........ 424/440; 424/650; 424/447; 424/464; 424/441; 424/43

(58) Field of Classification Search ................. None
See application file for complete search history.

(56) References Cited

U.S. PATENT DOCUMENTS

| | | | |
|---|---|---|---|
| 4,529,593 A | 7/1985 | Warrell, Jr. | |
| 5,258,376 A | 11/1993 | Bernstein | |
| 5,556,645 A * | 9/1996 | Bockman et al. | 424/650 |
| 5,574,027 A | 11/1996 | Bernstein | |
| 5,747,482 A | 5/1998 | Bernstein | |
| 5,883,088 A | 3/1999 | Bernstein | |
| 5,902,825 A | 5/1999 | Wie | |
| 5,968,922 A | 10/1999 | Bernstein | |
| 5,981,518 A | 11/1999 | Bernstein | |
| 5,998,397 A | 12/1999 | Bernstein | |
| 6,004,951 A | 12/1999 | Bernstein | |
| 6,048,851 A | 4/2000 | Bernstein | |
| 6,087,354 A | 7/2000 | Bernstein | |
| 2003/0083308 A1 * | 5/2003 | Bernstein | 514/45 |
| 2004/0014750 A1 | 1/2004 | Michaelis et al. | |
| 2005/0147662 A1 | 7/2005 | Freeman, Jr. | |
| 2007/0098815 A1 | 5/2007 | Bernstein | |

FOREIGN PATENT DOCUMENTS

| | | |
|---|---|---|
| WO | WO 91/17751 A1 | 11/1991 |
| WO | WO 00/40269 A2 | 7/2000 |
| WO | WO 01/24799 A1 | 4/2001 |
| WO | WO 2005/058331 A1 | 6/2005 |
| WO | WO 2007/100382 A2 | 9/2007 |

OTHER PUBLICATIONS http://www.ninds.nih.gov/disorders/peripheralneuropathy/detail_peripheralneuropathy.htm, Nov. 2, 2009.*
Eby, G. (2005) Elimination of arthritis pain and inflammation for over 2 years with a single 90 min, topical 14% gallium nitrate treatment: Case reports and review of actions of gallium III. Medical Hypotheses 65:1136-1141.
Bernstein et al., *Chemistry and Pharmacokinetics of Gallium Maltolate, a Compound with High Oral Gallium Bioavailability*, Metal Based Drugs 7(1):33-47 (2000).
Cavenagh, J. et al. (2006) Neuropathic pain: are we out of the woods yet? Internal Medicine Journal 36(4):251-255.
Campbell, J.N. and Meyer, R.A. (2006) Mechanisms of neuropathic pain. Neuron 52(1):77-92.
Kehlet, H. et al. (2006) Persistent postsurgical pain: risk factors and prevention. Lancet 367(9522):1618-1625.
Johnson, R.W. and McElhaney, J. (2009) Postherpetic neuralgia in the elderly. The International Journal of Clinical Practice 63(9):1386-1391.
Oaklander, A.L. (2008) Mechanisms of pain and itch caused by herpes zoster (shingles). The Journal of Pain 9(1 Suppl 1):S10-S18.
Pavan-Langston, D. (2008) Herpes zoster antivirals and pain management. Ophthalmology 115:S13-S20.
Li, Q. et al. (2009) Antiviral treatment for preventing postherpetic neuralgia (review). Cochrane Database of Systematic Reviews 2009, Issue 2, Art. No. CD006866.
Weinberg, J.M. (2007) Herpes zoster: Epidemiology, natural history, and common complications. Journal of the American Academy of Dermatology 57:S130-S135.

* cited by examiner

*Primary Examiner* — Ernst Arnold
*Assistant Examiner* — Hong Yu

(57) ABSTRACT

Provided are methods of treating pain, including neuropathic pain, in human and veterinary individuals. These methods employ locally administrable pharmaceutical gallium compositions, including pharmaceutical gallium compositions suitable for administration to the skin and mucous membranes. The compositions comprise pharmaceutically acceptable gallium compounds, such as gallium maltolate or gallium nitrate, together with pharmaceutically acceptable carriers suitable for local administration, including those suitable for topical administration. The administration of such compositions provides relief from pain, itching, allodynia, hyperalgesia, and related symptoms.

13 Claims, No Drawings

LOCAL ADMINISTRATION OF GALLIUM COMPOSITIONS TO TREAT PAIN

CROSS REFERENCE TO RELATED PATENT APPLICATIONS

This application claims priority under 35 U.S.C. §119(e) to U.S. Provisional Application No. 60/858,182, filed on Nov. 9, 2006, which is incorporated by reference in its entirety herein.

TECHNICAL FIELD

This invention relates generally to treatments for pain, including neuropathic pain. In particular, this invention pertains to pharmaceutical gallium compositions and their uses in treating pain by local administration.

BACKGROUND OF THE INVENTION

Gallium compounds, including gallium nitrate, gallium sulfate, and gallium maltolate, have been repeatedly shown to have anti-inflammatory activities when administered systemically (i.e., orally, intravenously, or by other means that introduce gallium into the bloodstream and allow for its distribution through the body). Particular efficacy for gallium has been reported in animal models of rheumatoid arthritis (Delbarre F. Rabaud M, COMPTES RENDUS DE L=ACADÉMIE DES SCIENCES, SERIES D 283:1469-1472, 1976; Matkovic V et al., CURRENT THERAPEUTIC RESEARCH 50:255-267, 1991; U.S. Pat. No. 5,175,006 to Matkovic et al.), multiple sclerosis (Whitacre C et al., JOURNAL OF NEUROIMMUNOLOGY 39:175-182, 1992), uveitis (Lobanoff M C et al., EXPERIMENTAL EYE RESEARCH 65:797-801, 1997), and Type 1 diabetes (Flynn J O et al., DIABETES 41:38 A, 1992). Systemically administered gallium has also shown efficacy in the treatment of cancer and infectious disease (Bernstein L R, PHARMACOLOGICAL REVIEWS 50:665-682, 1998). Locally administered gallium is effective in treating psoriasis and related dermatologic disorders (U.S. Pat. No. 5,747,482 to Bernstein). It has now been surprisingly discovered that locally administered gallium can reduce pain, itching, allodynia, hyperalgesia, and related symptoms.

Locally administered gallium is particularly effective in relieving neuropathic symptoms, especially peripheral neuropathic pain. Peripheral neuropathic pain is apparently caused by damage to peripheral neurons, and is typically characterized as "burning," "shooting," "stabbing," or "electric-shock-like." It may occur without external stimulation or, very commonly, it may be manifested as allodynia (an experience of pain from normally non-painful stimuli, such as from light touching) or hyperalgesia (an exaggerated sense of pain from a normally painful stimulation). The pain can be very intense and disabling; the pain from trigeminal neuralgia (neuropathy of the trigeminal nerve) is considered among the most severe types of pain known.

At least two million adults are estimated to have neuropathic pain in the United States, with the great majority having peripheral rather than central neuropathic pain (Morely-Forster P. PAIN RESEARCH MANAGEMENT 11 Suppl A:5A-10A, 2006). Some of the most common causes of peripheral neuropathic pain are diabetes, HIV infection, postherpetic neuralgia, trigeminal neuralgia, cancer, and cancer treatments. Numerous other causes of peripheral neuropathic pain are also known, including trauma, non-HIV infections, drugs, toxins, surgery, and complex regional pain syndrome (also called causalgia or reflex sympathetic dystrophy syndrome). The etiology for many cases of peripheral neuropathic pain is never discovered. Some of the common causes of peripheral neuropathic pain are summarized below.

PAINFUL DIABETIC NEUROPATHY: Diabetes afflicts about 21 million people in the United States (National Institute of Diabetes and Digestive and Kidney Diseases, NATIONAL DIABETES STATISTICS FACT SHEET: GENERAL INFORMATION AND NATIONAL ESTIMATES ON DIABETES IN THE UNITED STATES, 2005) and nearly 200 million people worldwide (Wild S et al., DIABETES CARE 27:1047-1053, 2004). Painful diabetic neuropathy is estimated to affect approximately 20-24% of diabetics, with pain being defined as a recording by the patient of at least 10 mm on a 100 mm visual analog pain scale (Schmader K E, THE CLINICAL JOURNAL OF PAIN 18:350-354, 2002). The pain occurs most commonly in the extremities.

CANCER AND CANCER-ASSOCIATED IATROGENIC NEUROPATHIC PAIN: Neuropathic pain is estimated to afflict about a third of cancer patients (Davis M P, Walsh D, AMERICAN JOURNAL OF HOSPICE PALLIATIVE CARE 21:137-142, 2004). In most cases the neuropathic pain is due to tumor tissue infiltrating or pressing on neurons, with other causes including nerve damage caused by surgery, chemotherapy, or radiotherapy. Treatments for breast cancer are particularly likely to cause neuropathic pain: nearly 50% of patients experience chronic pain following surgery for breast cancer, with most of the pain being neuropathic (Morely-Forster P. PAIN RESEARCH MANAGEMENT 11 Suppl A:5A-10A, 2006).

HIV-INFECTION RELATED NEUROPATHIC PAIN: Neuropathic pain, generally due to distal sensory polyneuropathy, is estimated to afflict at least a third of those infected with HIV (Luciano C A et al., CURRENT OPINION IN NEUROLOGY 16:403-409, 2003). The cause is not always known, but may be due to HIV infection of neurons, the release of neurotoxins by macrophages, toxic reactions to drugs, opportunistic infections, or nutrient deficiencies. Neuropathic pain associated with HIV infection appears to be an under-recognized and under-treated condition.

POSTHERPETIC NEURALGIA: Herpes zoster infection (shingles) is estimated to strike about 800,000 people each year in the United States (Schmader K E, THE CLINICAL JOURNAL OF PAIN 18:350-354, 2002). Pain associated with shingles is itself neuropathic, at least in part. The incidence of subsequent postherpetic neuralgia (nearly always a peripheral neuropathy) is directly correlated with age and with the severity of the herpetic rash. For herpes zoster patients over 50 years old (the great majority of herpes zoster patients), postherpetic neuralgia occurs in 50-68% one month after rash healing, in 25-50% three months after rash healing, and in 15-35% six months after rash healing (the lower numbers being for those treated with antiviral drugs) (Schmader K E, THE CLINICAL JOURNAL OF PAIN 18:350-354, 2002).

Peripheral neuropathic pain is clearly a widespread medical problem, occurring in millions of people worldwide, resulting from a wide range of causes.

Current Treatments for Peripheral Neuropathic Pain

Current preferred therapies for peripheral neuropathic pain include systemic antidepressants (particularly tricyclic antidepressants), anticonvulsants (including carbamazepine and gabapentin), opioid analgesics (including oxycodone, methadone, and dextromethorphan), and topical lidocaine and capsaicin. Few of these treatments produce even moderate pain relief for half the patients receiving them.

ANTIDEPRESSANTS: Antidepressants are commonly the first choice for treating neuropathic pain. A recent survey of the literature (Saarto T. Wiffen P J, THE COCHRANE DATABASE OF SYSTEMATIC REVIEWS 2005(3):CD005454, 2005) found that tricyclic antidepressants were the most effective, with amitriptyline being particularly effective. Amitriptyline, however, had an NNT (number needed to treat) value of 2 for moderate pain relief (that is, only 50% of those treated had at least moderate pain relief). In general, moderate pain relief for peripheral neuropathic pain was produced by tricyclic antidepressants in about 33-50% of patients, by serotonin noradrenaline reuptake inhibitors in about 20-25% of patients, and by selective serotonin reuptake inhibitors in about 14% of patients (Sindrup S H et al., BASIC & CLINICAL PHARMACOLOGY & TOXICOLOGY 96:399-409, 2005).

ANTICONVULSANTS: A number of anticonvulsants have been administered for the treatment of peripheral neuropathic pain, with gabapentin, carbamazepine, and phenyloin appearing to be the most effective. Again, however, the efficacy rates are fairly low. For moderate pain relief, gabapentin had an NNT of 3.2 in postherpetic neuralgia; in painful diabetic neuropathy it had an NNT of 3.8, while carbamazepine had an NNT of 2.3 and phenyloin had an NNT of 2.1 (Wiffen P et al., THE COCHRANE DATABASE OF SYSTEMATIC REVIEWS 2005 (3):CD001133, 2005). Other tested anticonvulsants appeared to be less effective. It is noted that anticonvulsants, as tricyclic antidepressants, frequently produce significant adverse effects in patients.

OPIOID ANALGESICS: A recent meta-analysis of the efficacy and safety of opioid agonists in the treatment of non-malignant neuropathic pain showed marginal to no efficacy in short-term (24 hour) studies, and marginal efficacy in intermediate-term (8-56 day) studies (Eisenberg E et al., JAMA 293:3043-3052, 2005). The drugs studied were morphine, oxycodone, methadone, and levorphanol. A study of levorphanol found that patients with postherpetic neuralgia had an average 14% reduction in pain with a low dose, and a 33% reduction with a high dose, though 31% of the subjects dropped out of the study due to drug side effects (Rowbotham M C et al., NEW ENGLAND JOURNAL OF MEDICINE 348:1223-1232, 2003). All the opioid drugs commonly produced significant but non-life-threatening adverse effects.

TOPICAL LIDOCAINE: A topically applied patch containing 5% lidocaine is commonly used to treat localized peripheral neuropathic pain. Clinical studies have shown that this treatment results in modest reductions of pain for many patients (e.g., Argoff C E et al., CURRENT MEDICAL RESEARCH AND OPINION 20 Suppl 2:S21-S28, 2004). One controlled study found an NNT of 2 in postherpetic neuralgia (Hempenstall K et al., PLoS MEDICINE 2:e164, 2005). To remain effective, the patches must be changed several times per day. The patches cause numbness of the contacted skin, and commonly cause skin irritation, and usually do not relieve severe pain.

TOPICAL CAPSAICIN: An analysis of two studies on the use of topical capsaicin cream to treat postherpetic neuralgia found a low efficacy rate, with an NNT value of 3.26 (Hempenstall K et al., PLoS MEDICINE 2:e164, 2005). It is noted that placebo-controlled studies with capsaicin are compromised due to the clearly noticeable sensations (including pain) produced in the skin by capsaicin; thus, perceived efficacy of capsaicin may benefit from a placebo effect.

Many other systemic and local treatments are used in attempts to relieve peripheral neuropathic pain, generally with no more than moderate success. Recently, subcutaneously injected botulinum-A toxin has been tried in a small number of patients with trigeminal neuralgia (Piovesan E J et al., NEUROLOGY 66:1458-1459, 2006) and in a single patient with postherpetic neuralgia (Liu H T et al., PAIN MEDICINE 7:89-91, 2006). The patient with postherpetic neuralgia reported pain relief for several weeks after numerous injections, followed by a recurrence of pain at pre-treatment levels. The patients with trigeminal neuralgia reported transient low to moderate pain relief following multiple injections, with side effects including muscle weakness.

It is thus apparent that currently available treatments for peripheral neuropathic pain have only low to moderate efficacy, and many patients are left without significant pain relief. The lack of adequate pain relief for millions of people with peripheral neuropathic pain, as well as for those with other types of pain, represents a great unmet medical need.

SUMMARY OF THE INVENTION

Accordingly, it is a primary object of the invention to provide pharmaceutical compositions, methods, and drug delivery systems for treating pain, including allodynia, hyperalgesia, paresthesia, discomfort, itching, and neuropathic pain.

In a preferred embodiment of the invention, a method is provided in which pain is treated in an individual afflicted with such a condition, comprising administering to the painful region, to tissues adjacent to the painful region, or to tissues in or adjacent to the region from which the pain is referred, a therapeutically effective amount of a pharmaceutical composition comprising a pharmaceutically acceptable gallium compound and a carrier suitable for local administration.

Additional objects, advantages and novel features of the invention will be set forth in part in the description which follows, and in part will become apparent to those skilled in the art upon examination of the following, or may be learned by practice of the invention.

DETAILED DESCRIPTION OF THE INVENTION

Before the present compositions, methods, and drug delivery systems of the invention are disclosed and described, it is to be understood that this invention is not limited to specific formulations, i.e., specific carrier materials or the like, to specific dosage regimens, or to specific drug delivery systems, as such may vary. It is also to be understood that the terminology used herein is for the purpose of describing particular embodiments only and is not intended to be limiting.

As used herein (which includes the specifications and the claims), the term "pain" encompasses the usual meanings of the word, and also encompasses the usual meanings of "itching," "allodynia," "hyperalgesia," "paresthesia," and "discomfort," as well as combinations of these.

As used herein, the singular forms "a," "an," and "the" include plural referents unless the context clearly dictates otherwise. Thus, for example, reference to "a gallium compound" includes mixtures of such compounds; reference to "a carrier" includes mixtures of two or more carriers; and the like.

The term "topical administration" is used herein in its conventional sense to mean delivery of a pharmacologically active agent to the skin or mucosa, including the mucosa of the mouth, nasal and sinus cavities, eyes, gastrointestinal tract, bladder, urethra, and vagina.

The term "local administration" as used herein encompasses the meaning of "topical administration," and also includes administration to spatially restricted portions of the body, including portions of the skin, muscle, eyes, and other tissues and organs, and combinations of these.

The term "patient" as used herein is meant to include a human or a veterinary patient. Within the context of the present invention, veterinary patients include both mammalian and non-mammalian veterinary patients, the latter including such veterinary patients as, for example, lizards and birds.

The terms "active agent," "drug," and "pharmacologically active agent" are used interchangeably herein to refer to a chemical material or compound that, when administered to an organism (human or animal), induces a desired pharmacologic effect, such as a reduction in pain.

The terms "to treat" and "treatment" as used herein encompass the usual meanings of these terms plus the usual meanings of the terms "to prevent" and "prevention". Thus, for example, "treatment" of postherpetic neuralgia, as the term "treatment" is used herein, encompasses both prevention of postherpetic neuralgia in a predisposed individual and treatment of postherpetic neuralgia in an individual who has such a disease.

By the term "effective" amount of a drug is meant a sufficient amount of a compound to provide the desired effect and performance at a reasonable benefit/risk ratio as attends any medical treatment.

The term "vehicle" or "carrier" as used herein refers to a vehicle suitable for administration of a drug, and includes any such materials known in the art, e.g., any liquid or non-liquid carrier, gel, cream, ointment, lotion, paste, emulsifier, solvent, liquid diluent, solid, wax, powder, or the like, that is stable with respect to all components of the pharmaceutical formulation, and is appropriate and safe for the particular mode of administration for which it is intended (e.g., topical, subcutaneous, intramuscular, intravenous, intraocular).

This invention comprises pharmaceutical compositions suitable for the localized administration of gallium, and devices and methods for using such compositions to treat pain. Formulations appropriate for application to skin, mucous membranes, the eyes, or other external or internal portions of the body may be prepared in the practice of the invention.

Treatment is applicable to human and veterinary patients, including particularly mammals and birds. Mammalian veterinary subjects include, without limitation, dogs, cats, and members of the Equidae, Bovidae, Caprinae, and Suidae. Veterinary subjects also include, without limitation, reptiles, amphibians, and fish.

The locally administrable pharmaceutical compositions comprise a carrier and a pharmaceutically acceptable gallium compound. Carriers suitable for localized administration include, for example, topical carriers for topical administration, subcutaneous carriers for subcutaneous injection, intraocular carriers for intraocular administration, and the like, as are well known in the art. Locally administrable pharmaceutical compositions suitable for topical administration, which is a preferred means of administration, comprise a topical carrier and a pharmaceutically acceptable gallium compound.

A topical carrier, as noted above, is one that is generally suited to topical drug administration and includes any such materials known in the art. The topical carrier is selected so as to provide the composition in the desired form, e.g., as a liquid, lotion, cream, paste, gel, gum, powder, ointment, or soluble solid, and may be comprised of a material of either naturally occurring or synthetic origin, or of a combination. It is essential that the selected carrier not adversely affect the active agent or other components of the topical formulation. Examples of suitable topical carriers for use herein include water, alcohols and other nontoxic organic solvents, glycerin, mineral oil, silicone, petroleum jelly, petrolatum, lanolin, fatty acids, sugars, vegetable oils, parabens, waxes, and the like. The composition of the invention may be administered in the form of a shampoo, in which case conventional components of such a formulation are included as well, e.g., surfactants, conditioners, viscosity modifying agents, humectants, and the like. The composition of the invention may also be prepared, without limitation, as lozenges, troches, candies, orally disintegrating tablets, sublingual tablets, buccal tablets, buccal patches, chewing gums, and the like, as well as suppositories and the like, as nasal sprays and the like, as eye drops and the like, as lip balms and the like, and as tablets and capsules and the like.

Particularly preferred formulations herein are colorless, odorless ointments, lotions, creams, and gels.

Ointments are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating, and nonsensitizing. As explained in REMINGTON: THE SCIENCE AND PRACTICE OF PHARMACY, 19th Ed. (Easton, Pa.: Mack Publishing Co., 1995), at pages 1399-1404, ointment bases may be grouped in four classes: oleaginous bases, emulsifiable bases, emulsion bases, and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin, and hydrophilic petrolatum. Emulsion ointment bases are either water-in-oil emulsions or oil-in-water emulsions, and include, for example, cetyl alcohol, glyceryl monostearate, lanolin, and stearic acid. Preferred water-soluble ointment bases are prepared from polyethylene glycols of varying molecular weight; again, reference may be had to REMINGTON: THE SCIENCE AND PRACTICE OF PHARMACY, $20^{th}$ Edition (Gennaro A R, Ed., Lippincott, Williams and Wilkins, 2000) for further information. A particularly preferred ointment base for use in conjunction with the present invention contains a hydrophilic petrolatum such as that which may be obtained under the trademark Aquaphor® from Beiersdorf, Inc. (Wilton, Conn.).

Lotions are preparations to be applied to the skin surface without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethylcellulose, or the like.

Creams containing the selected gallium compound are, as known in the art, viscous liquid or semisolid emulsions, either oil-in-water or water-in-oil. Cream bases are water-washable, and contain an oil phase, an emulsifier, and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington (2000) supra, is generally a nonionic, anionic, cationic, or amphoteric surfactant.

Gel formulations are preferred for application to the scalp. As will be appreciated by those working in the field of topical drug formulation, gels are semisolid, suspension-type systems. Single-phase gels contain organic macromolecules distributed substantially uniformly throughout the carrier liquid, which is typically aqueous, but also, preferably, contain an alcohol and, optionally, an oil.

The gallium compositions of the invention may also be formulated using liposomes. Such formulations may be particularly advantageous for sustained release or delayed release compositions. Other formulations for sustained release or delayed release may also be employed.

Shampoos for treating peripheral neuropathic pain may be formulated with the selected gallium compound and standard shampoo components, i.e., cleansing agents, thickening agents, preservatives, and the like, with the cleansing agent representing the primary ingredient, typically an anionic surfactant or a mixture of an anionic and an amphoteric surfactant.

Various additives, known to those skilled in the art, may be included in the topical or other local formulations of the invention. For example, solvents may be used to dissolve certain drug substances. Other optional additives include skin permeation enhancers, opacifiers, colorants, fragrances, flavoring agents, anti-oxidants, gelling agents, thickening agents, stabilizers, preservatives, and the like. The topical or other local compositions of the invention may be also optionally comprise one or more other active agents, including, without limitation, pain-reducing agents, analgesics, anesthetics, anti-inflammatory agents, anti-seizure agents, antidepressants, anticancer agents, antibiotics, antimicrobial agents, antibacterial agents, antifungal agents, antiviral agents, antiparasitic agents, and anthelmintic agents.

In the preferred topical and other local formulations of the invention, the gallium compound is present in an amount such that the gallium content is generally about 0.00001 to about 15 percent by weight of the formulation, preferably about 0.001 to about 0.5 percent, and most preferably about 0.01 to about 0.1 percent.

As an example of a pharmaceutically acceptable aqueous solution of the invention, gallium nitrate is dissolved in water, at a gallium concentration of from about 0.01 to about 15 wt. % Ga, preferably from about 1 to about 10 wt. % Ga, and most preferably from about 2 to about 7 wt. % Ga. As another example of a pharmaceutically acceptable aqueous solution of the invention, which is preferred, gallium maltolate is dissolved in water at a concentration of about 0.0005 to about 1 wt. % Ga, preferably about 0.01 to about 0.16 wt. % Ga. Other excipients, carriers, stabilizers, solubilizers, buffers, pH adjusters, permeation enhancers, absorption enhancers, thickeners, active agents, preservatives, etc. may be added to the solutions. An example of a possible additive is DMSO.

The topical compositions of the invention may also be delivered to the skin using "transdermal"-type patches, wherein the drug composition is contained within a laminated structure that serves as a drug delivery device to be affixed to the skin. In such a structure, the drug composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. The particular polymeric adhesive selected will depend on the particular drug, vehicle, etc., i.e., the adhesive must be compatible with all components of the drug-containing composition. In an alternative embodiment, the drug-containing reservoir and skin contact adhesive are present as separate and distinct layers, with the adhesive underlying the reservoir that, in this case, may be either a polymeric matrix as described above, or it may be a liquid or hydrogel reservoir, or it may take some other form.

The backing layer in these laminates, which serves as the upper surface of the device, functions as the primary structural element of the laminated structure, and provides the device with much of its flexibility. The material for the backing material should be selected so that it is substantially impermeable to the drug and to any other components of the drug-containing composition, thus preventing loss of any components through the upper surface of the device. The backing layer may be either occlusive or non-occlusive, depending on whether it is desired that the skin become hydrated during drug delivery. The backing is preferably made of a sheet or film of a preferably flexible elastomeric material. Examples of polymers that are suitable for the backing layer include polyethylene, polypropylene, polyesters, and the like.

During storage and prior to use, the laminated structure includes a release liner. Immediately prior to use, this layer is removed from the device to expose the basal surface thereof, either the drug reservoir or a separate contact adhesive layer, so that the system may be affixed to the skin. The release liner should be made from a drug/vehicle impermeable material.

Such devices may be fabricated using conventional techniques, known in the art, for example by casting a fluid admixture of adhesive, drug, and vehicle onto the backing layer, followed by lamination of the release liner. Similarly, the adhesive mixture may be cast onto the release liner, followed by lamination of the backing layer. Alternatively, the drug reservoir may be prepared in the absence of drug or excipient, and then loaded by "soaking" in a drug/vehicle mixture.

As with the other topical formulations of the invention, the drug composition contained within the drug reservoirs of these laminated system may contain a number of components. In some cases, the drug may be delivered "neat," i.e., in the absence of additional liquid. In most cases, however, the drug will be dissolved, dispersed, or suspended in a suitable pharmaceutically acceptable vehicle, typically a solvent or gel. Other components that may be present include preservatives, stabilizers, surfactants, and the like.

Formulations employed for transdermal patches of the invention typically contain about 0.0005 to about 10 wt. % Ga, preferably about 0.01 to about 2 wt. % Ga, and most preferably about 0.05 to about 0.5 wt. % Ga.

The topical formulations, including those used in conjunction with the laminated drug delivery systems, may in addition contain a skin permeation enhancer. Because the inherent permeability of the skin to some drugs may be too low to allow therapeutic levels of the drug to pass through a reasonably sized area of unbroken skin, it is necessary to co-administer a skin permeation enhancer with such drugs. Suitable enhancers are well know in the art and include, for example, dimethylsulfoxide (DMSO), dimethyl formamide (DMF), N,N-dimethylacetamide (DMA), decylmethylsulfoxide ($C_{10}$MSO), $C_2$-$C_6$ alkanediols, and the 1-substituted azacycloheptan-2-ones, particularly 1-n-dodecylcyclazacycloheptan-2-one (available under the trademark AZONE® from Whitby Research Incorporated, Richmond, Va.), alcohols, bases, and the like.

In a methodological embodiment of the invention, pain, including peripheral neuropathic pain, is treated by locally administering a pharmaceutical composition comprising gallium to a painful region, to tissues adjacent to the painful region, or to tissues in or adjacent to the region from which the pain is referred. By "adjacent" is meant within a few millimeters to within a few centimeters. A preferred means of local administration is topical administration. In this methodological embodiment, a topical pharmaceutical composition comprising gallium is topically administered to the skin or mucous membrane at a region of pain, or at a region in which pain is present in underlying tissues. Topical administration may also be applied to a region of skin or mucus membrane from which pain is referred, or that is superior to underlying tissues from which pain is referred. Treatable pain may originate, or seem to originate, in the skin or mucous membrane, or in underlying tissue or tissues. The underlying tissue or tissues may include, without limitation, muscle, tendon, ligament, bone, cartilage, nerve, organ, vascular, follicular, glandular, connective, and joint tissues. Treatable individuals include humans, but also include veterinary subjects. When used in a preventive method, susceptible regions are treated prior to the occurrence of pain on regions known to be susceptible to pain in a particular individual.

The composition may be applied by any practical, medically acceptable means. For example, application may be made using fingers, swabs, droppers, squeeze tubes or bottles, compresses, patches, osmotic pumps, aerosols, means for injection, or other means. In the treatment of pain, including peripheral neuropathic pain, it will be recognized by those skilled in the art that the optimal quantity and spacing of individual dosages of the gallium compositions of the invention will be determined by the nature and extent of the condition being treated, the form, route and site of administration, and the particular individual undergoing treatment, and that such optimums can be determined by conventional techniques. It will also be appreciated by one skilled in the art that the optimal dosing regimen, i.e., the number of doses of a gallium composition of the invention, can be ascertained using conventional course of treatment determination tests. Generally, a dosing regimen will involve administration of the selected formulation at least once daily, and preferably one to four times daily, until the pain, itching, paresthesia, or other symptoms have subsided. In some cases, a single dose will suffice, while in other cases dosing may continue for days, weeks, months, years, or indefinitely, to maintain adequate pain relief.

The area of the body to be treated may also be soaked in a solution of the invention. Such soaking may be particularly useful in treating pain of the hands, arms, feet, or legs. Soaking may be continuous for as much as several days, or may be applied daily for about 1 minute to about 12 hours, preferably for about 15 minutes to 6 hours, and most preferably for about 1 hour to 3 hours. An example of such a soaking solution is gallium maltolate dissolved in water at a gallium concentration of about 0.0005 to about 1 wt. % Ga, preferably about 0.01 to about 0.16 wt. % Ga. Excipients, carriers, stabilizers, solubilizers, buffers, pH adjusters, permeation enhancers, absorption enhancers, thickeners, active agents, preservatives, colorants, fragrances, etc. may be added to the solution. The soaking solution may be at room temperature or at other comfortable temperatures, including comfortably elevated temperatures.

Other forms of administration of the compositions of the invention include, without limitation, buccal, sublingual, lingual, intra-lingual, nasal, intra-sinus, intraocular, topical ocular, oral, topical to the lips, vaginal, urethral, perianal, instillation into the bladder, rectal, otic, local perfusion into tissue by injection, subcutaneous, intramuscular, peritoneal, intravenous, intra-arterial, and by inhalation.

Typical topical doses of the gallium composition, expressed as the amount of contained elemental gallium per square centimeter of surface area (as on the skin or mucosal surface) are, for example, about 0.000001 to 1 mg, preferably about 0.0001 to 0.1 mg, and more preferably about 0.0005 to 0.005 mg; such doses are typically administered, for example, once per week to six times per day, and more typically one to four times per day. When administered continuously, as by the use of a patch or osmotic pump, typical daily doses of the gallium composition, expressed as the amount of contained elemental gallium per square centimeter of surface area (as on the skin) are, for example, about 0.000005 to 5 mg, preferably about 0.0005 to 0.5 mg, and more preferably about 0.001 to 0.05 mg. Typical doses of the gallium composition, expressed as the amount of contained elemental gallium, when administered to a spatially restricted internal portion of the body, as by injection or other means, are, for example, about 0.000001 to 5 mg, preferably about 0.002 to 0.5 mg, and more preferably about 0.01 to 0.1 mg per cubic centimeter of tissue.

Pain treatable by this invention (which includes itching, allodynia, hyperalgesia, paresthesia, and discomfort, as well as combinations of these) is not restricted to any particular cause, disease, or disorder. Examples of treatable pain include, without limitation, neuropathic pain; pain associated with inflammation, including that from arthritis, hemorrhoids, or plantar fasciitis as examples; pain associated with trauma, injury, surgery, infection (e.g., bacterial, viral, fungal, protozoan, helminthic, parasitic), neoplasia, hyperplasia, radiation, irritation, or burns; pain associated with locally or systemically contacted toxins; pain associated with insect, spider, or animal bites or stings; and pain associated with allergic or other sensitivity reactions, pruritus, and the like. Furthermore, peripheral neuropathic pain treatable by this invention is not restricted to any particular cause, disease, or disorder. Examples of treatable peripheral neuropathic pain include, without limitation, painful diabetic neuropathy; infection-related neuropathic pain, including HIV-related neuropathic pain, herpes zoster related neuropathic pain, and herpes simplex related neuropathic pain; postherpetic neuralgia; facial neuralgia, including trigeminal neuralgia; cancer-associated neuralgia, including neuralgia caused by neuronal tumors, tumor infiltration of neurons, tumors pressing on neurons, chemotherapy, surgery, and radiation treatment; pain associated with trauma, including that caused by surgery; pain associated with root avulsions, nerve entrapment, carpal tunnel syndrome, or ischemic nerve injury; painful traumatic mononeuropathy or polyneuropathy; distal sensory polyneuropathy; complex regional pain syndrome; and neuropathy caused by systemic or locally contacted toxins.

Gallium compounds usable in this invention include, without limitation, gallium nitrate, gallium sulfate, gallium citrate, gallium chloride, gallium complexes of 3-hydroxy-4-pyrones including gallium maltolate, gallium pyridinones, gallium tartrate, gallium succinate, gallium gluconate, gallium palmitate, gallium 8-quinolinolate, gallium porphyrins including gallium(III) protoporphyrin IX, gallium transferrin, bis(2-acetylpyridine 4N-dimethylthiosemicarbazone) gallium (III)-gallium(III) tetrachloride, gallium pyridoxal isonicotinoyl hydrazone, gallium complexes of kenpaullone and its derivatives, and any other pharmaceutically acceptable gallium inorganic salts, organic salts, inorganic compounds, chelates, coordination compounds, complexes, and organometallic compounds. Gallium maltolate, tris(3-hydroxy-2-methyl-4H-pyran-4-onato)gallium, is a preferred gallium compound of the invention; this compound is described, for example, in U.S. Pat. No. 5,981,518 to Bernstein.

The practice of the present invention will employ, unless otherwise indicated, conventional techniques of drug formulation, which are within the skill of the art. Such techniques are fully explained in the literature. See, for example, REMINGTON: THE SCIENCE AND PRACTICE OF PHARMACY (2000), cited supra, as well as Goodman & Gilman's THE PHARMACOLOGICAL BASIS OF THERAPEUTICS, 9th Ed. (New York: McGraw-Hill, 1996) and Ansel et al., PHARMACEUTICAL DOSAGE FORMS AND DRUG DELIVERY SYSTEMS, $6^{th}$ Ed. (Media, Pa.: Williams & Wilkins, 1995). Any suitable pharmaceutical formulations that comprise pharmaceutically acceptable gallium compositions may be utilized in the practice of the invention.

All patents, patent documents, and publications cited herein are hereby incorporated by reference in their entirety for their disclosure concerning any pertinent information not explicitly included herein.

It is to be understood that while the invention has been described in conjunction with the preferred specific embodiments thereof, the foregoing description, as well as the examples that follow, are intended to illustrate and not limit the scope of the invention. Other aspects, advantages, and modifications will be apparent to those skilled in the art to which the invention pertains.

EXPERIMENTAL

The following examples are put forth so as to provide those of ordinary skill in the art with a complete disclosure and description of how to make and use the compositions of the invention. The examples are intended as non-limiting examples of the invention. While efforts have been made to ensure accuracy with respect to variables such as amounts, temperature, etc., experimental error and deviations should be taken into account. Unless indicated otherwise, parts are parts by weight, temperature is degrees Celsius, and pressure is at or near atmospheric. All components were obtained commercially unless otherwise indicated.

Example 1

Topical Formulation of Gallium Maltolate I

A gallium maltolate formulation for topical application to the skin was prepared at room temperature with the following composition:
 Gallium maltolate: 0.25 wt %
 AQUAPHOR®: 89.75 wt %
 Water (sterile, deionized): 10 wt %
First, 5 g of gallium maltolate powder was stirred in 200 g of water for 120 min. This solution/suspension was then slowly added to 1795 g of AQUAPHOR®, over a period of 10 min, with continuous stirring. Stirring then continued for an additional 30 minutes, until a homogeneous white cream was produced.

Example 2

Topical Formulation of Gallium Maltolate II

A gallium maltolate formulation for topical application to the skin was prepared at room temperature with the following composition:
 Gallium maltolate: 0.5 wt %
 AQUAPHOR®: 49.5 wt %
 Water (sterile, deionized): 50 wt %
First, 4 g of gallium maltolate powder was stirred in 400 g of water for 120 min. This solution was then slowly added to 396 g of AQUAPHOR®, over a period of 10 min, with continuous stirring. Stirring then continued for an additional 30 minutes, until a homogeneous white cream was produced.

Example 3

Use of Gallium Maltolate Cream to Treat Postherpetic Neuralgia

A 100-year-old woman had been experiencing postherpetic neuralgia with erythema on the left side of her face for approximately three years. The pain was so severe that it interfered with sleep and other daily activities. During that period she had tried numerous systemic analgesics to relieve the pain, including amitriptyline 25 mg BID, methadone 5 mg BID, carbamazepine 100 mg BID, gabapentin 200 mg QD, oxycodone 20 mg BID, naproxen, acetaminophen, and intravenous hydrogen peroxide. She had also tried topically applied medications, including lidocaine 5% patches. None of these treatments produced significant pain relief. She then began treatment using the topical gallium maltolate formulation of Example 1, above. This formulation was applied three times per day to the affected area, at about 8 AM, 1 PM, and 9 PM, every day for four weeks. The formulation was administered by dipping a fingertip lightly into the formulation, and then smearing the formulation from the fingertip onto the affected area. Approximately 15 minutes following the initial administration, significant reduction of pain was noticed. Three days following the start of treatment, the pain had been further reduced, as had the erythema. The reduction in pain and erythema continued for the entire four week treatment period. No adverse effects from the treatment were observed. The patient reported that the pain relief she experienced while using topical gallium maltolate had greatly improved her quality of life.

Example 4

Use of Gallium Maltolate Cream to Treat Pain and Itching Associated with Vaginal Inflammation A 49-year-old woman had vaginal inflammation associated with moderate to severe pain, itching, and erythema. Topical miconazole was ineffective and irritating, and topical benzocaine had little effect. Light topical application of the gallium maltolate formulation of Example 2 to the vagina and immediately adjacent external region relieved the pain, itching, and erythema within 15 minutes. Continued use of the formulation three times per day eliminated the vaginal inflammation in two days. No adverse effects from the treatment were observed.

Example 5

Use of Gallium Maltolate Cream to Treat Inflamed Painful Spider Bites

A 100-year-old woman received two spider bites on the inner surface of her lower left arm. The bites became inflamed, with erythema, edema, and severe pain. The pain was severe enough to disrupt sleep. The woman applied the topical gallium maltolate formulation of Example 1 to the inflamed, painful areas of skin at and around the bites. The formulation was administered by dipping a fingertip lightly into the formulation, and then smearing the formulation from the fingertip onto the affected areas. The pain was entirely relieved with ten minutes following application of the gallium maltolate formulation, and the erythema and edema subsided within an hour. No adverse effects from the treatment were observed.

Example 6

Use of Gallium Maltolate Cream to Treat Pain and Inflammation Associated with a Herpes Simplex Lesion A 48-year-old woman developed an active herpes simplex lesion (cold sore), 5 mm across, just above her left upper lip. About 24 hours after it was first noticed, the lesion had become a painful weeping abscess that was very painful to the touch. A small amount of the formulation of Example 2 was applied to the lesion at this time, and was then applied twice per day thereafter for four days. Twelve hours after the initial application, the pain and inflammation associated with the lesion were greatly reduced. After four days, all pain and discomfort associated with the lesion had gone, and the lesion itself had largely healed, with almost no remaining inflammation. The patient said that such lesions normally take more than ten days to resolve, with pain being present until full resolution.

I claim:

1. A method for treating peripheral neuropathic pain associated with postherpetic neuralgia in an individual afflicted with such a condition, comprising administering locally to the painful region, to tissues adjacent to the painful region, or to tissues in or adjacent to the region from which the pain is referred, a pharmaceutical composition comprising a therapeutically effective amount of a pharmaceutically acceptable gallium compound selected from the group consisting of gallium sulfate, gallium citrate, gallium chloride, gallium complexes of 3-hydroxy-4-pyrones including gallium maltolate, gallium pyridinones, gallium tartrate, gallium succinate, gallium gluconate, gallium palmitate, gallium 8-quinolinolate, gallium porphyrins, gallium transferrin, and gallium pyridoxal isonicotinoyl hydrazone, and a carrier suitable for local administration.

2. The method of claim 1, wherein the pharmaceutical composition is selected from the group consisting of an ointment, a lotion, a cream, and a gel.

3. The method of claim 1, wherein the pharmaceutical composition is a shampoo.

4. The method of claim 1, wherein the pharmaceutical composition is present in a drug reservoir contained within a laminated patch adapted to be affixed to the skin.

5. The method of claim 1, wherein the pharmaceutical composition is selected from the group consisting of a lozenge, a troche, a candy, an orally disintegrating tablet, a sublingual tablet, a buccal tablet, a buccal patch, a nasal spray, an aerosol, a lip balm, and chewing gum.

6. The method of claim 1, wherein the pharmaceutical composition is in the form of eye drops.

7. The method of claim 1, wherein the pharmaceutical composition is administered by soaking.

8. The method of claim 1, wherein the means of administration of the pharmaceutical composition is selected from the group consisting of buccal, sublingual, lingual, intra-lingual, nasal, intra-sinus, intraocular, topical ocular, oral, topical to the lips, vaginal, otic, local perfusion into tissue by injection, subcutaneous, intramuscular, peritoneal, and inhalation.

9. The method of claim 1, wherein the gallium content of the pharmaceutical composition represents about 0.00001 to about 15 percent by weight of the composition.

10. The method of claim 1, wherein the gallium content of the pharmaceutical composition represents about 0.001 to about 0.5 percent by weight of the composition.

11. The method of claim 1, wherein the gallium content of the pharmaceutical composition represents about 0.01 to about 0.1 percent by weight of the composition.

12. The method of claim 1, wherein the gallium compound is a gallium complex of a 3-hydroxy-4-pyrone.

13. The method of claim 1, wherein the gallium complex of a 3-hydroxy-4-pyrone is gallium maltolate.

* * * * *